United States Patent
Ziegler et al.

(10) Patent No.: US 7,906,141 B2
(45) Date of Patent: *Mar. 15, 2011

(54) SUSTAINED-RELEASE, ORAL PHARMACEUTICAL FORMS OF FORMULATION

(75) Inventors: Iris Ziegler, Rott-Roetgen (DE); Johannes Bartholomaeus, Aachen (DE)

(73) Assignee: Gruenenthal GmbH, Aachen (DE)

( * ) Notice: Subject to any disclaimer, the term of this patent is extended or adjusted under 35 U.S.C. 154(b) by 883 days.

This patent is subject to a terminal disclaimer.

(21) Appl. No.: 10/084,676

(22) Filed: Feb. 28, 2002

(65) Prior Publication Data

US 2003/0044464 A1 Mar. 6, 2003

Related U.S. Application Data

(63) Continuation of application No. PCT/EP00/07525, filed on Aug. 3, 2000.

(30) Foreign Application Priority Data

Aug. 31, 1999 (DE) .................................. 199 40 944

(51) Int. Cl.
*A61K 9/22* (2006.01)
*A61K 9/52* (2006.01)
*A61K 31/135* (2006.01)

(52) U.S. Cl. .................. 424/468; 424/457; 514/649

(58) Field of Classification Search .................. 424/451, 424/489, 464, 468, 470, 474, 457, 458, 459, 424/462, 463, 475, 490; 514/649
See application file for complete search history.

(56) References Cited

U.S. PATENT DOCUMENTS

| 5,516,803 | A | * | 5/1996 | Raffa | 514/570 |
| 5,776,492 | A | * | 7/1998 | Betzing et al. | 424/465 |
| 5,914,129 | A | * | 6/1999 | Mauskop | 424/464 |
| 5,958,452 | A | * | 9/1999 | Oshlack et al. | 424/457 |

FOREIGN PATENT DOCUMENTS

| DE | 19927688 A1 | 12/2000 |
| EP | 0546676 A1 | 6/1993 |

OTHER PUBLICATIONS

Remington's Pharmaceutical Sciences, (Alfonso R. Gennaro, edited), p. 1641-1647 (1990).*
Remington's Pharmaceutical Sciences, (Alfonso R. Gennaro, edited), pp. 1641-1647 (1990).*

* cited by examiner

*Primary Examiner* — Blessing M Fubara
(74) *Attorney, Agent, or Firm* — Crowell & Moring LLP

(57) ABSTRACT

A sustained-release, oral pharmaceutical formulation of tramadol comprising a compound formed in situ of tramadol or its salt and a pharmaceutically acceptable acidic substance. The compound formed in situ has a desired water solubility. Also provided are methods of treatment using the pharmaceutical formulations. Method for preparing such formulations are also provided. The preparation method comprises repeatedly mixing tramadol or its salt with the acidic substance, and moistening the mixture and formulating the mixture under an energy input, such as heat or pressure. Optionally, drying, repeated granulating, extrusion and pelleting may also be included.

2 Claims, No Drawings

SUSTAINED-RELEASE, ORAL PHARMACEUTICAL FORMS OF FORMULATION

CROSS REFERENCE TO RELATED APPLICATIONS

The present application is a continuation of international patent application no. PCT/EP00/07525, filed Aug. 3, 2000, designating the United States of America, the entire disclosure of which is incorporated herein by reference. Priority is claimed based on Federal Republic of Germany patent application no. 199 40 944.7, filed Aug. 31, 1999.

BACKGROUND OF THE INVENTION

The present invention relates to partially sustained-release, oral pharmaceutical forms of administration in which the active substance, tramadol, is present at least partially as a compound formed in situ which has a water solubility of $\leq 100$ mg/ml, and to processes for their preparation.

The administration of pharmacological active substances in the form of sustained-release preparations represents a therapeutic improvement for many active substances, especially analgesics. Even for pharmacological substances with a relatively short half-life in vivo, retardation of release makes it possible to provide a preparation with a long-lasting action and also, through more constant blood levels, to avoid side effects and improve the patients' observance of dosage instructions.

The release of pharmacologically active substances can be retarded e.g. by embedding in a sustained-release matrix or by coating with sustained-release film.

The retardation of the release of very readily water-soluble active substances, e.g. tramadol hydrochloride, an analgesic for controlling intense to very intense pain, with the aid of film coatings is often complex and unsatisfactory because film coatings for such active substances frequently constitute an inadequate diffusion barrier or the permeability of these film coatings changes during storage (P. B. O'Donnell, J. W. McGinity, "Mechanical Properties of Polymeric Films, Prepared from Aqueous Polymeric Dispersions in Aqueous Polymeric Coatings for Pharmaceutical Dosage Forms", Drugs and the Pharmaceutical Science, vol. 79, ed. J. W. McGinity, Marcel Decker, New York, Basle, Hong Kong 1997).

The manufacture of preparations with sustained-release film coatings applied water-soluble ingredients therefore requires expensive coating processes with multilayer films or time-consuming curing processes, as described in U.S. Pat. No. 5,645,858, U.S. Pat. No. 5,580,578, U.S. Pat. No. 5,681,585 or U.S. Pat. No. 5,472,712, in K. Bauer, "Coated Pharmaceutical Dosage Forms," Medpharm Scientific Publishers, Stuttgart 1998, B. Sutter, Thesis, University of Dusseldorf, 1987, or in F. N. Christensen, Proceed. Intern. Symp. Contr. Rel. Bioact. Mater. 17, 124, 1990.

It is also possible to retard the release of pharmaceutically active substances by reducing their solubility, e.g. by forming sparingly soluble salts (H. Sucker, Pharmazeutische Technologie (Pharmaceutical Technology), Georg Thieme Verlag, Stuttgart, N.Y. 1991). In some cases, however, the use of such sparingly soluble salts in forms of administration requires very complex processes to prepare these salts.

The object of the present invention was therefore to provide pharmaceutical formulations which do not exhibit the above disadvantages.

SUMMARY AND DETAILED DESCRIPTION OF THE INVENTION

Surprisingly, it has now been found that this object is achieved by the preparation of at least partially sustained-release, oral pharmaceutical formulations of tramadol, in which the sustained-release portion of the active substance is present as a compound, formed in situ, of tramadol and another active substance and/or auxiliary substance with a water solubility of $\leq 100$ mg/ml.

The water solubility of the compound formed in situ is preferably $\leq 50$ mg/ml, particularly preferably $\leq 30$ mg/ml and very particularly preferably $\leq 10$ mg/ml.

To prepare the compound formed in situ, the active substance tramadol, preferably as a water-soluble salt and particularly preferably as tramadol hydrochloride, is reacted with a water-soluble, pharmaceutically acceptable salt of another, acidic pharmaceutical active substance or auxiliary substance which forms with tramadol a compound with a water solubility of $\leq 100$ mg/ml, preferably $\leq 50$ mg/ml, particularly preferably $\leq 30$ mg/ml and very particularly preferably $\leq 10$ mg/ml. These compounds are classified as sparingly water-soluble compounds.

In the context of this specification, in situ formation means that the tramadol or a water-soluble salt thereof is mixed with another, acidic pharmaceutical active substance or auxiliary substance or water-soluble salts thereof, preferably during the preparation of the pharmaceutical formulation according to the invention, moistened several times and optionally extruded or formulated energy input.

As the water-soluble salt of the other, acidic pharmaceutical active substance and/or biocompatible auxiliary substance for the preparation of the tramadol compound formed in situ, the sodium salt of diclofenac, naproxen, acetylsalicylic acid, salicylic acid, benzoic acid, saccharin, cyclamate or acesulfame is preferably used.

The sustained-release, oral pharmaceutical formulation according to the invention can contain the tramadol component and the other pharmaceutical active substance and/or auxiliary substance in any suitable molar ratio.

In one preferred embodiment of the pharmaceutical formulation according to the invention, the tramadol component is in excess and is released at two or more different rates. This means that, in addition to the retarded release of tramadol from the compound formed in situ, part of the tramadol component is released rapidly as an initial dose.

In another preferred embodiment of the pharmaceutical formulation according to the invention, the tramadol component and the other, acidic pharmaceutical active substance or auxiliary substance are in a molar ratio such that, despite the possible difference in their original water solubilities, the two active substances or the active substance/auxiliary substance undergo retarded release at the same rate.

In one particularly preferred embodiment of the pharmaceutical formulation according to the invention, tramadol hydrochloride and diclofenac sodium are reacted in situ to give rise a very sparingly soluble compound with a water solubility of $\leq 0.3$ mg/ml. The proportions of tramadol to diclofenac in these formulation are preferably from 0.5:1 to 4:1 and particularly preferably from 1:1 to 2:1. Tramadol is preferably used in excess for the in situ reaction with diclofenac so that, in these formulation, an initial dose of tramadol is released rapidly and afterwards tramadol and diclofenac undergo retarded release at the same rate. A rapid alleviation of pain can be achieved by the tramadol released immediately as an initial dose. The slow release of the active substances from the sustained-release form then enables the analgesic action to be maintained over a longer period.

Other preferred sustained-release pharmaceutical formulation according to the invention contain a compound which has been formed in situ from equimolar amounts of tramadol and diclofenac so that the total amount of each active substance undergoes retarded release at the same rate.

The at least partially sustained-release, oral formulations of tramadol according to the invention are preferably multiparticulate formulations, particularly preferably in the form of granules, microparticles, microtablets or pellets and very particularly preferably in the form of pellets, optionally filled into capsules. The pellets are preferably produced by extrusion and spheronization and preferably have a diameter of 0.1 to 3 mm.

The forms of administration according to the invention can also be formulated as coated tablets or ordinary tablets, preferably as rapidly disintegrating tablets. The tablets can comprise compressed pellets which particularly preferably are of the rapidly disintegrating type.

One particular advantage of the formulations according to the invention is that the tramadol is already retarded during the preparation by the in situ formation of a compound of tramadol and another active substance and/or auxiliary substance with a water solubility of ≦100 mg/ml, without the use of a sustained-release matrix and/or a sustained-release coating.

The pharmaceutical formulations according to the invention preferably have at least one enteric coating which dissolves as a function of pH. Because of this coating, said forms pass through the stomach undissolved and the active substance(s) and/or auxiliary substance(s) only undergo controlled release in the intestinal tract. The enteric coating can be applied from aqueous solution or dispersion and/or from organic solution. It preferably dissolves at a pH of between 5 and 7.

The enteric coating preferably consists of shellac, polymethacrylic acid/ethyl acrylate or methacrylic acid/methyl acrylate/methyl methacrylate copolymer, methacrylic acid/methyl methacrylate copolymers, hydroxypropyl methyl cellulose acetate-succinate, cellulose acetate-phthalate, polyvinyl acetate-phthalate, hydroxypropyl methyl cellulose phthalate and/or cellulose acetate-trimellitate.

Further retardation of release over and above that caused in situ, and hence a further modification of the release of the tramadol and optionally other active substances, can be effected by a variety of methods known to those skilled in the art.

Preferably, a further retardation can be effected with the aid of sustained-release coatings. Suitable sustained-release coatings include water-insoluble waxes or polymers, e.g. acrylic resins, preferably poly(meth)acrylates, or water-insoluble celluloses, preferably ethyl cellulose. These materials are known to those of ordinary skills in the art, e.g. Bauer, et al., "Überzogene Arzneiformen" ("Coated Pharmaceutical Forms"), Wissenschaftliche Verlagsgesellschaft mbH Stuttgart, 1988, p. 69 et seq., which is incorporated herein by reference and thus forms part of the disclosure.

To adjust the rate of release of the active substances, the sustained-release coatings can optionally contain, in addition to the water-insoluble polymers, non-retarding, preferably water-soluble polymers in amounts of up to 30 wt. %, such as polyvinylpyrrolidone or water-soluble celluloses, preferably hydroxypropyl methyl cellulose or hydroxypropyl cellulose, and/or hydrophilic pore-forming agents such as sucrose, sodium chloride or mannitol, and/or plasticizers known in the art.

To further retard the release of the sparingly soluble tramadol compound formed in situ, the pharmaceutical formulations according to the invention can preferably also contain said compound in a sustained-release matrix, preferably as a uniform distribution.

Matrix materials which can be used for instant invention include physiologically compatible, hydrophilic materials known to those skilled in the art. The hydrophilic matrix materials used are preferably polymers and particularly preferably cellulose ethers, cellulose esters and/or acrylic resins. The matrix materials used are very particularly preferably ethyl cellulose, hydroxypropyl methyl cellulose, hydroxypropyl cellulose, hydroxymethyl cellulose, poly(meth)acrylic acid and/or derivatives thereof such as their salts, amides or esters.

Other preferred matrix materials include hydrophobic materials such as hydrophobic polymers, waxes, fats, long-chain fatty acids, fatty alcohols or corresponding esters or ethers, or mixtures thereof. The hydrophobic materials used are particularly preferably C12-C30 fatty acid mono- or diglycerides and/or C12-C30 fatty alcohols and/or waxes, or mixtures thereof.

The sustained-release matrix material used can also be mixtures of said hydrophilic and hydrophobic materials. The release of the active substances will preferably be adjusted so that the pharmaceutical formulations according to the invention have to be taken at most twice a day and particularly preferably only once a day. With the knowledge of the action of analgesics, those ordinarily skilled in the art are aware of the doses in which they are to be used in order to achieve the desired effect.

Another possible way of modifying the release of the active substance tramadol and optionally other active substances from the pharmaceutical formulations according to the invention is by varying their surface area and/or by using hydrophilic auxiliary substances. The effect of enlarging the surface area, e.g. by using smaller pellets, is to increase the rate of release of the active substances. The result of increasing the amount of hydrophilic auxiliary substances, e.g. lactose, in the pellet core is again to increase the rate of release of the active substance(s).

The pharmaceutical formulations according to the invention are suitable for the control of pain or for the treatment of urinary incontinence, coughs, inflammatory and/or allergic reactions, depression, drug and/or alcohol abuse, gastritis, diarrhea, cardiovascular disease, respiratory disease, mental illness or epilepsy.

The invention also provides processes for the preparation of the at least partially sustained-release, oral pharmaceutical formulations according to the invention, wherein tramadol or a salt thereof, and another acidic pharmaceutical active substance or auxiliary substance or water-soluble salts thereof, and optionally other auxiliary substances, are mixed, moistened several times and formulated under an energy input.

The mixture is preferably moistened each time with aqueous media and particularly preferably with water or aqueous binder solutions. The energy input preferably takes the form of pressure and/or heat.

In one preferred embodiment of the process according to the invention, the mixture is moistened and granulated several times, extruded at least once and then optionally converted to the final formulation.

The mixture is preferably extruded and/or dried after each moistening and granulation step.

After these moistening, granulation, extrusion and/or drying steps, the mixture is preferably pelleted, optionally mixed with other auxiliary substances and then compressed to tablets. Pelleting is preferably preceded by extrusion.

In one particularly preferred embodiment of the process according to the invention, the moistened mixture of salts is granulated, extruded, moistened and granulated again, extruded and then rounded. In another particularly preferred process, the moistened mixture is granulated, dried, moistened and granulated again, extruded and then rounded.

The pellets are preferably provided with an enteric coating before being compressed.

In one particularly preferred embodiment of the process according to the invention, tramadol hydrochloride and diclofenac sodium are used to prepare the compound formed in situ.

The pharmaceutical formulation according to the invention may be converted to the final formulation, by various methods known to those skilled in the art.

Depending on the embodiment, the pharmaceutical formulation according to the invention can also contain, as additional constituents, the conventional auxiliary substances and additives known to those skilled in the art. If the pharmaceutical formulation according to the invention have coatings, these can be applied by conventional processes, e.g. by the coating pan process, by the spraying of solutions, dispersions or suspensions, by the hot-melt process or by the powder application process.

Surprisingly, a feature of the pharmaceutical formulation according to the invention is that the release of the active substance tramadol and optionally other active substances from the pharmaceutical formulation according to the invention is not affected by changes of conventional release conditions, such as the ion concentration of the buffers, the presence of surface-active substances, the use of different types of buffer and/or the application of different mechanical stresses. Even after prolonged storage at an elevated temperature of up to 40° C., the rates of release of the active substance(s) from the pharmaceutical formulation according to the invention do not change. The release profile exhibited by the pharmaceutical formulations obtained is stable on storage.

This release of the active substances from the at least partially sustained-release, oral, pharmaceutical formulations according to the invention follows kinetics which otherwise can only be achieved by complex and expensive matrix systems. Surprisingly, it is found that the release of the pharmaceutical active substances can be retarded without using conventional sustained-release systems, so the release profiles can be modulated by varying the size of the pharmaceutical formulation and incorporating soluble auxiliary substances, while maintaining the common rate of release of the two active substances. Surprisingly, despite the very small particle size averaging ≦5 μm, the release of the two active substances from the sparingly soluble tramadol/diclofenac compounds prepared in situ is retarded to the same extent as the release of separately prepared formulation of salts of tramadol and diclofenac which is identical except for its substantially larger particle sizes of approx. 20-100 μm.

As the release of the active substance tramadol and optionally other active substances from the pharmaceutical formulations according to the invention can be retarded without using additional sustained-release systems, the pharmaceutical formulations can be produced in less time and at less expense with excellent reproducibility.

The solubility of the compounds of tramadol and the other, corresponding, acidic pharmaceutical active substance or auxiliary substance was determined as follows:

The pellets in question, produced by the process according to the invention and not provided with a sustained-release coating, containing a compound of tramadol, i.e. (1RS,2RS)-2-[(dimethylamino)methyl]-1-(3-methoxyphenyl)cyclohexanol, and the appropriate acidic pharmaceutical active substance or auxiliary substance, were placed in deionized water at 25° C. in an amount corresponding to approx. 25 mg of pellets to 5 ml of deionized water, with shaking for 24 hours (Vibrax, shaker bath setting=1200 at 25° C.) such as to form a saturated solution at this temperature.

The corresponding saturation solubility range was estimated in preliminary experiments using the separately prepared salt of tramadol and the appropriate acidic pharmaceutical active substance or auxiliary substance.

After letting the saturated solution settle, the clear supernatant was pipetted off and centrifuged for 5 minutes at 3500 rpm. Part of the resulting clear supernatant is then transferred to an HPLC sample vial and the concentration of the compound of tramadol and the appropriate acidic pharmaceutical active substance or auxiliary substance is determined against tramadol hydrochloride as standard.

The release profile of the preparations of the Examples was determined as follows:

The preparations were tested either in a spinning cage apparatus (See Examples 1 to 6) or in a paddle stirrer (See Example 7), as described in the European Pharmacopoeia, at a temperature of 37° C. (±0.5° C.) and a speed of rotation of 100 min-1 or 50 min-1. In Example 1, the preparation was tested for ten hours, in Example 6 for five hours and in Example 5 for four hours in 900 ml of artificial intestinal juice without enzymes (pH 7.2). In Examples 2 to 4 and 7, the preparation was tested first for two hours in 600 ml of artificial gastric juice without enzymes (pH 1.2) and then for a further eight hours in 900 ml of artificial intestinal juice without enzymes (pH 7.2).

The amount of active substances released at any given time was determined by HPLC. The values and curves show an average of 3 samples in each case.

The invention is illustrated below with the aid of the Examples. The illustrations are given solely by way of example and do not limit the general spirit of the invention.

EXAMPLES

Example 1

125 g of tramadol hydrochloride, 125 g of diclofenac sodium and 250 g of microcrystalline cellulose (Avicel PH 101, FMC) were homogeneously mixed in a Kenwood Chef mixer for 10 minutes and then granulated with water in an amount sufficient for moistening. The sticky lumpy mass of granules was then extruded in a Nica extruder (type E140) with a 1.0 mm extrusion die. While the rods of extrudate were initially still extremely sticky, they changed in the course of the extrusion process to a very dry extrudate with insufficient plasticity for subsequent spheronization. The extrudate was moistened and granulated again. The resulting granules were extruded again in the Nica extruder and the moist extrudate was then converted to round pellets of uniform size in a Nica spheronizer (type S450). The pellets were dried in a drying cabinet at a temperature of approx. 50° C. and fractionated into sieve fractions, ≧90% of the pellets falling within the desired sieve class of 800-1250 μm.

Composition of the Pellets:

| | | |
|---|---|---|
| Tramadol-HCl | 50 mg | |
| Diclofenac-Na | 50 mg | |
| Microcrystalline cellulose (Avicel PH 101, FMC) | 100 mg | |
| Total | 200 mg | |

For the pellets produced above, the water solubility of the active substance tramadol from the compound formed in situ was found to be 0.36 mg/ml, as determined by the method indicated above.

The release profile, determined by the method indicated above, was as follows:

| | Amount in mg released from 200 mg of pellets | |
|---|---|---|
| Time in min | for tramadol | for diclofenac |
| 30 | 10 | 7 |
| 120 | 18 | 15 |
| 300 | 26 | 24 |
| 600 | 35 | 33 |

Example 2

200 g of tramadol hydrochloride, 100 g of diclofenac sodium, 22 g of powdered succinic acid and 332 g of microcrystalline cellulose (Avicel PH 101, FMC) were homogeneously mixed in a Kenwood Chef mixer for 10 minutes and processed to pellets analogously to Example 1.

Composition of the Pellets:

| | |
|---|---|
| Tramadol hydrochloride | 100 mg |
| Diclofenac sodium | 50 mg |
| Succinic acid, powdered | 11 mg |
| Microcrystalline cellulose (Avicel PH 101, FMC) | 166 mg |
| Total | 327 mg |

500 g of the classified pellets were then provided with an enteric coating in a fluidized at an air inlet temperature of 40° C. with an aqueous shellac solution, the amount of shellac applied being 5 wt. %, based on the weight of the pellets.

Film Coating for 500 g of Pellets:

| | |
|---|---|
| Aqueous shellac solution ASL 125 (20% solids content, Marchand & Cie) | 125 g |
| Triethyl citrate | 1.25 g |
| Water | 136.25 g |

The release profile, determined as indicated above, was as follows:

| | Amount in mg released from 344 mg of pellets | |
|---|---|---|
| Time in min | for tramadol | for diclofenac |
| 120 | 0 | 0 |
| 240 | 61 | 10 |
| 480 | 76 | 25 |
| 600 | 84 | 28 |

Example 3

1.25 kg of tramadol hydrochloride, 1.25 kg of diclofenac sodium, 1.0 kg of lactose monohydrate, 0.75 kg of microcrystalline cellulose (Avicel PH 101, FMC) and 0.75 kg of colloidal microcrystalline cellulose (Avicel RC 591, FMC) were mixed in a Diosna (type P25) and granulated. The pellets were produced analogously to Example 1 with the following changes. The sticky moist granules were not extruded after granulation, but spread directly onto metal trays sealed with foil and heated for 20 minutes in a drying cabinet at 50 to 70° C., thereby avoiding moisture losses. The granules were then moistened and granulated again. They were extruded in a Nica extruder (type E140) with a 0.8 mm extrusion die. The extrudate was spheronized in a Nica spheronizer (type S450). After the pellets had been dried in a drying cabinet, they were classified, ≧90% of the pellets falling in the desired sieve class of between 0.63 and 1.0 mm.

Composition of the Pellets:

| | |
|---|---|
| Tramadol hydrochloride | 75 mg |
| Diclofenac sodium | 75 mg |
| Lactose monohydrate | 60 mg |
| Microcrystalline cellulose (Avicel PH 101, FMC) | 45 mg |
| Colloidal microcrystalline cellulose (Avicel RC 591, FMC) | 45 mg |
| Total | 300 mg |

5 kg of the pellets were then coated in a Hüttlin spherical coater at an air inlet temperature of 40° C. with 21 wt. % of Eudragit L-55, based on the total weight of the pellets, from an aqueous dispersion of the following composition:

Film Coating for 5 kg of Pellets:

| | |
|---|---|
| Eudragit L30D-55 (Röhm, 30% aqueous dispersion of 1:1 polymethacrylic acid/ethyl acrylate copolymer) | 3500 g |
| Eudragit NE30D (Röhm, 30% aqueous dispersion of polyethyl acrylate/methyl methacrylate copolymer) | 315 g |
| Triethyl citrate | 175 g |
| Talcum, micronized | 262.5 g |
| Water | 3657.5 g |

Composition of the Capsules:

400 mg of the coated pellets, together with 46 mg of tramadol initial-dose pellets (corresponding to 25 mg of tramadol hydrochloride, 10.5 mg of Avicel PH 105 and 10.5 mg of l-HPC LH31), were filled into size 0 hard gelatin capsules on a Zanasi E6 encapsulating machine with 2 pellet dispensing stations.

The release profile, determined as indicated above, was as follows:

| Time in min | Amount in mg released per capsule | |
|---|---|---|
| | for tramadol (100 mg dose) | for diclofenac (75 mg dose) |
| 30 | 25 | 0 |
| 120 | 28 | 0 |
| 240 | 56 | 29 |
| 480 | 79 | 50 |
| 600 | 85 | 56 |

Example 4

1.5 kg of tramadol hydrochloride, 1.0 kg of diclofenac sodium, 1.0 kg of lactose monohydrate, 0.75 kg of microcrystalline cellulose (Avicel PH 101, FMC) and 0.75 kg of colloidal microcrystalline cellulose (Avicel RC 591, FMC) were mixed in a Diosna (type P25) and granulated. The pellets were produced analogously to Example 3 with the following changes. The reaction of the diclofenac sodium with the tramadol hydrochloride took place directly after the first granulation, in the mixer, by heating the jacket to a temperature of 70° C. for 30 min, the stirrer blade being switched on for a few brief periods. After the reaction, the second granulation was carried out directly without emptying.

Composition of the Pellets:

| | |
|---|---|
| Tramadol hydrochloride | 75 mg |
| Diclofenac sodium | 50 mg |
| Lactose monohydrate | 50 mg |
| Microcrystalline cellulose (Avicel PH 101, FMC) | 37.5 mg |
| Colloidal microcrystalline cellulose (Avicel RC 591, FMC) | 37.5 mg |
| Total | 250 mg |

5 kg of pellets were then coated in a Hüttlin spherical coater at an air inlet temperature of 40° C. with 22 wt. % of Eudragit L-55, based on the total weight of the pellets, from an aqueous dispersion of the following composition:

Film Coating for 5 kg of Pellets:

| | |
|---|---|
| Eudragit L30D-55 (Röhm, 30% aqueous dispersion of 1:1 polymethacrylic acid/ethyl acrylate copolymer) | 3667 g |
| Triethyl citrate | 220 g |
| Talcum, micronized | 550 g |
| Water | 4913.5 g |

Composition of the Capsules:

348 mg of the coated pellets, together with 46 mg of tramadol initial-dose pellets (corresponding to 25 mg of tramadol hydrochloride, 10.5 mg of Avicel PH 105 and 10.5 mg of l-HPC LH31), were filled into size 0 hard gelatin capsules on a Zanasi E6 encapsulating machine with 2 pellet dispensing stations.

The release profile, determined as indicated above, was as follows:

| Time in min | Amount in mg released per capsule | |
|---|---|---|
| | for tramadol dose (100 mg) | for diclofenac dose (50 mg) |
| 30 | 27 | 0 |
| 120 | 32 | 0 |
| 240 | 78 | 24 |
| 480 | 94 | 40 |
| 600 | 99 | 45 |

Example 5

100 g of tramadol hydrochloride, 69 g of saccharin sodium and 169 g of microcrystalline cellulose (Avicel PH 101, FMC) were homogeneously mixed in a Kenwood Chef mixer for 10 minutes and then processed to pellets analogously to Example 1.

Composition of the Pellets:

| | |
|---|---|
| Tramadol hydrochloride | 100 mg |
| Saccharin sodium | 69 mg |
| Microcrystalline cellulose (Avicel PH 101, FMC) | 169 mg |
| Total | 338 mg |

The release profile, determined as indicated above, was as follows:

| Time in min | Proportion released in % for tramadol |
|---|---|
| 30 | 84 |
| 120 | 100 |
| 240 | 104 |

Example 6

100 g of tramadol hydrochloride, 84 g of naproxen sodium and 184 g of microcrystalline cellulose (Avicel PH 101, FMC) were homogeneously mixed in a Kenwood Chef mixer for 10 minutes and then processed to pellets analogously to Example 1.

Composition of the Pellets:

| | |
|---|---|
| Tramadol hydrochloride | 100 mg |
| Naproxen sodium | 84 mg |
| Microcrystalline cellulose (Avicel PH 101, FMC) | 184 mg |
| Total | 368 mg |

The release profile, determined as indicated above, was as follows:

| Time in min | Proportion released in % | |
|---|---|---|
| | for tramadol | for naproxen |
| 30 | 72 | 55 |
| 120 | 91 | 88 |
| 240 | 101 | 100 |
| 300 | 102 | 102 |

1.5 kg of tramadol hydrochloride, 1.0 kg of diclofenac sodium, 1.0 kg of lactose monohydrate, 0.75 kg of microcrystalline cellulose (Avicel PH 101, FMC) and 0.75 kg of colloidal microcrystalline cellulose (Avicel RC 591, FMC) were homogeneously mixed in a Diosna (type P25) for 10 minutes and processed to pellets analogously to Example 3.

Composition of the Pellets:

| | |
|---|---|
| Tramadol hydrochloride | 75 mg |
| Diclofenac sodium | 50 mg |
| Lactose monohydrate | 50 mg |
| Microcrystalline cellulose (Avicel PH 101, FMC) | 37.5 mg |
| Colloidal microcrystalline cellulose (Avicel RC 591, FMC) | 37.5 mg |
| Total | 250 mg |

5 kg of pellets were then coated in a Hüttlin spherical coater at an air inlet temperature of 40° C. with 21 wt. % of Eudragit L-55, based on the total weight of the pellets, from an aqueous dispersion of the following composition:

Film Coating for 5 kg of Pellets:

| | |
|---|---|
| Eudragit L30D-55 (Röhm, 30% aqueous dispersion of 1:1 polymethacrylic acid/ethyl acrylate copolymer) | 3500 g |
| Eudragit FS 30D (Rohm, 30% aqueous dispersion of polymethacrylic acid/methyl acrylate/methyl methacrylate copolymer) | 350 g |
| Triethyl citrate | 210 g |
| Glycerol monostearate (Cutina GMS, Henkel) | 92.4 g |
| Water | 3134.6 g |

322.5 mg of pellets, corresponding to a dose of 75 mg of tramadol hydrochloride and 50 mg of diclofenac sodium, were subsequently mixed first with 22.5 mg of crosslinked polyvinylpyrrolidone (Kollidon CL, BASF) and then with 205.6 mg of Cellactose (Meggle), 25 mg of tramadol hydrochloride and 1.4 mg of magnesium stearate and compressed to 7×14 mm notched oblong tablets weighing 577 mg. These disintegrate back to the individual pellets in an aqueous medium.

The release profile, determined as indicated above, was as follows:

| | Amount in mg released per tablet | |
|---|---|---|
| Time in min | for tramadol dose (100 mg) | for diclofenac dose (50 mg) |
| 30 | 25 | 0 |
| 120 | 25 | 0 |
| 240 | 65 | 22 |
| 360 | 77 | 31 |
| 420 | 81 | 35 |
| 600 | 91 | 42 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed:

1. A sustained-release, oral pharmaceutical formulation of tramadol, comprising a compound of tramadol hydrochloride and diclofenac sodium, wherein said compound is formed in situ, said compound having a water solubility of $\leqq 100$ mg/ml, and wherein at least part of the tramadol at least part of the diclofenac are released at the same rate.

2. A method for preparing an oral pharmaceutical formulation, the method comprising:
   mixing tramadol hydrochloride and diclofenac sodium to form a mixture;
   moistening the mixture; and
   repeating the above mixing and moistening steps and formulating the mixture under an energy input.

\* \* \* \* \*